United States Patent
Tsai et al.

(10) Patent No.: US 10,521,895 B2
(45) Date of Patent: Dec. 31, 2019

(54) DYNAMIC AUTOMATIC FOCUS TRACKING SYSTEM

(71) Applicant: UTECHZONE CO., LTD., New Taipei (TW)

(72) Inventors: Hung-Ju Tsai, New Taipei (TW);
Chia-Liang Lu, New Taipei (TW);
Ming-Cheng Lai, New Taipei (TW);
Sheng-Chieh Lo, New Taipei (TW)

(73) Assignee: Utechzone Co., Ltd., New Taipei (TW)

( * ) Notice: Subject to any disclaimer, the term of this patent is extended or adjusted under 35 U.S.C. 154(b) by 431 days.

(21) Appl. No.: 15/355,611

(22) Filed: Nov. 18, 2016

(65) Prior Publication Data

US 2017/0169559 A1    Jun. 15, 2017

(30) Foreign Application Priority Data

Dec. 9, 2015   (TW) .............................. 104141274 A

(51) Int. Cl.
*H04N 5/225*   (2006.01)
*H04N 5/232*   (2006.01)
*G06T 7/00*    (2017.01)

(52) U.S. Cl.
CPC .......... *G06T 7/0004* (2013.01); *H04N 5/2256* (2013.01); *H04N 5/2257* (2013.01); *H04N 5/23212* (2013.01); *G06T 2207/30164* (2013.01)

(58) Field of Classification Search
CPC ..... G06T 7/0004; G01N 21/00; H04N 5/2256
See application file for complete search history.

(56) References Cited

U.S. PATENT DOCUMENTS

| 7,957,633 | B2* | 6/2011 | Uehara ..................... G02B 7/36 |
| | | | 348/349 |
| 8,106,997 | B2* | 1/2012 | Nagahata ........... H04N 5/23212 |
| | | | 348/345 |
| 8,599,283 | B2* | 12/2013 | Matsunaga ............ H04N 5/235 |
| | | | 348/218.1 |
| 9,049,364 | B2* | 6/2015 | Tseng .................. H04N 5/23293 |
| 9,110,035 | B2* | 8/2015 | Zheng ................... G01N 21/896 |
| 9,602,780 | B2* | 3/2017 | Ito ............................ G01N 21/47 |
| 9,716,824 | B2* | 7/2017 | Ito ....................... H04N 5/23212 |
| 10,147,625 | B2* | 12/2018 | Suzuki ................... H01L 21/677 |

(Continued)

FOREIGN PATENT DOCUMENTS

| CN | 101030252 A | 9/2007 |
| CN | 101339349 A | 1/2009 |

(Continued)

*Primary Examiner* — Irfan Habib
(74) *Attorney, Agent, or Firm* — Muncy, Geissler, Olds & Lowe, P.C.

(57) ABSTRACT

The present invention provides a dynamic automatic focus tracking system, comprising an image capturing device for capturing an image of a workpiece in a target picture-taking region; a driving device for adjusting a spacing between the image capturing device and the workpiece; and a focal length adjustment module coupled to the image capturing device and the driving device to generate a control signal according to a figure feature and a predefined figure feature in the image of the workpiece and send the control signal to the driving device, thereby adjusting a position of the image capturing device with the driving device.

10 Claims, 3 Drawing Sheets

(56) References Cited

U.S. PATENT DOCUMENTS

| | | | |
|---|---|---|---|
| 2004/0131244 A1* | 7/2004 | Nehse | G01B 11/024 382/141 |
| 2006/0238640 A1* | 10/2006 | Hofer | G03B 13/36 348/345 |
| 2006/0291845 A1* | 12/2006 | Sugimoto | G03B 13/34 396/122 |
| 2007/0073439 A1* | 3/2007 | Habibi | B25J 9/1697 700/213 |
| 2007/0206099 A1 | 9/2007 | Matsuo et al. | |
| 2008/0174771 A1 | 7/2008 | Yan et al. | |
| 2008/0187185 A1* | 8/2008 | Misawa | G06K 9/00228 382/118 |
| 2008/0297648 A1* | 12/2008 | Furuki | G02B 7/38 348/345 |
| 2009/0009651 A1 | 1/2009 | Takayanagi | |
| 2010/0241267 A1* | 9/2010 | Nishikawa | B23Q 17/20 700/195 |
| 2011/0001840 A1* | 1/2011 | Ishii | G02B 7/365 348/222.1 |
| 2011/0075151 A1* | 3/2011 | Jeong | G01N 21/956 356/453 |
| 2012/0194814 A1* | 8/2012 | Wang | G01J 3/021 356/301 |
| 2012/0218460 A1* | 8/2012 | Eichinger | G02B 21/244 348/345 |
| 2013/0194390 A1 | 8/2013 | Hirooka | |
| 2013/0208166 A1* | 8/2013 | Tseng | H04N 5/23212 348/333.11 |
| 2013/0235252 A1* | 9/2013 | Tseng | H04N 5/23212 348/349 |
| 2013/0286191 A1* | 10/2013 | Ito | G01N 21/47 348/131 |
| 2014/0043470 A1* | 2/2014 | Winterot | G02B 9/34 348/135 |
| 2015/0015696 A1* | 1/2015 | Delaney | H04N 5/23212 348/86 |
| 2015/0094599 A1* | 4/2015 | Kim | G02B 15/00 600/476 |
| 2015/0103156 A1* | 4/2015 | Northrup | G02B 21/365 348/79 |
| 2016/0193681 A1* | 7/2016 | Pesme | B23K 9/0956 219/130.01 |
| 2016/0343125 A1* | 11/2016 | Keitler | G01B 11/2513 |
| 2017/0045350 A1* | 2/2017 | Fiekers | G01B 21/047 |
| 2017/0248768 A1* | 8/2017 | Seitz | G06T 7/571 |
| 2018/0033697 A1* | 2/2018 | Suzuki | H01L 21/677 |

FOREIGN PATENT DOCUMENTS

| | | |
|---|---|---|
| CN | 101750714 A | 6/2010 |
| CN | 103226014 A | 7/2013 |
| CN | 103248816 A | 8/2013 |
| CN | 104597634 A | 5/2015 |
| JP | S6289010 A | 4/1987 |
| JP | H0384403 A | 4/1991 |
| JP | 2012127761 A | 7/2012 |
| TW | M249048 U | 11/2004 |
| TW | 200930062 A | 7/2009 |

* cited by examiner

DYNAMIC AUTOMATIC FOCUS TRACKING SYSTEM

BACKGROUND OF THE INVENTION

1. Technical Field

The present invention relates to automatic focus tracking systems and more particularly, to an automatic focus tracking system for use with a gas platform.

2. Description of Related Art

Precision inspection is usually applied to products which require high precision and low fault tolerance rate, performed in conjunction with an automated production line, and located at the end of a supply chain, so as to inspect the surfaces of finished products for defects, such as smears, abrasions and copper exposure. Precision inspection is usually carried out with an optical instrument, such as a line-scan camera or an area-scan camera, to capture images of the surface of a workpiece, and then defects, such as foreign bodies or pattern abnormalities, are identified by computer-based image processing technology.

An inspection process performed on precise workpieces, such as panels, entails conveying the workpieces with a conveyor belt. The workpieces must be prevented from being scratched or smeared by the conveyor belt and thus incurring defects. To this end, a gas platform is provided to carry some of the precise workpieces so that the workpieces are subjected to a positive pressure under which the workpieces are suspended and thereby prevented from coming into contact with a plane below. The workpieces being conveyed need to be inspected, even though the workpieces are suspended above the gas platform under a positive pressure provided by the gas platform, with a suspension height clearance of 300 um or so. However, conventional cameras have a depth of field of just 35 um and thus cannot capture images of an object not within the depth of field. In view of this, the gas platform inevitably requires a quick efficient focus tracking technique.

BRIEF SUMMARY OF THE INVENTION

The objective of the present invention is to overcome a drawback of the prior art, that is, conventional computation processes carried out to effectuate focusing are too complicated to achieve real-time focusing.

One aspect of the present invention is to provide a dynamic automatic focus tracking system, comprising: an image capturing device for capturing an image of a workpiece in a target region; a driving device for adjusting a spacing between the image capturing device and the workpiece; and a focal length adjustment module coupled to the image capturing device and the driving device to generate a control signal according to a figure feature and a predefined figure feature in the image of the workpiece and send the control signal to the driving device, thereby adjusting a position of the image capturing device with the driving device.

In a preferable embodiment, the dynamic automatic focus tracking system further comprises a gas platform for providing the workpiece with a positive pressure under which the workpiece is suspended above the gas platform.

In a preferable embodiment, the dynamic automatic focus tracking system further comprises an optical projector for projecting the figure feature onto the workpiece or to a vicinity of the workpiece.

In a preferable embodiment, the focal length adjustment module calculates a distance parameter between the image capturing device and a correct focal length position according to a ratio of the figure feature to the predefined figure feature and controls the driving device according to the distance parameter, thereby allowing the image capturing device to move to the correct focal length position.

In a preferable embodiment, the dynamic automatic focus tracking system further comprises a light module disposed between the image capturing device and the target region to provide coaxial light.

In a preferable embodiment, the light module comprises an illumination unit disposed beside the image capturing device and a spectroscope disposed between the image capturing device and the target region to reflect light off the illumination unit such that the light falls on the target region to form the coaxial light.

Another aspect of the present invention is to provide a dynamic automatic focus tracking system, comprising: a first image capturing device for obtaining an image of a workpiece in a target region and thus obtains an image of the workpiece; a second image capturing device for obtaining a figure feature on the workpiece or near the workpiece; a driving device for adjusting a spacing between the image capturing device and the workpiece; and a focal length adjustment module coupled to the second image capturing device and the driving device to generate a control signal according to the figure feature and a predefined figure feature in the image of the workpiece and send the control signal to the driving device, thereby adjusting a position of the image capturing device with the driving device.

In a preferable embodiment, the dynamic automatic focus tracking system further comprises a gas platform for providing the workpiece with a positive pressure under which the workpiece is suspended above the gas platform.

In a preferable embodiment, the dynamic automatic focus tracking system further comprises an optical projector for projecting the figure feature onto the workpiece or to a vicinity of the workpiece.

In a preferable embodiment, the focal length adjustment module calculates a distance parameter between the first image capturing device and a correct focal length position according to a ratio of the figure feature to the predefined figure feature and controls the driving device according to the distance parameter, thereby allowing the first image capturing device to move to the correct focal length position.

In a preferable embodiment, the dynamic automatic focus tracking system further comprises a light module disposed between the first image capturing device and the target region to provide coaxial light.

In a preferable embodiment, the light module comprises an illumination unit disposed beside the first image capturing device and a spectroscope disposed between the first image capturing device and the target region to reflect light off the illumination unit such that the light falls on the target region to form the coaxial light.

Therefore, the present invention attains the following benefits compared to the prior art:

1. A computation process of the present invention is simple enough to enable an image capturing device to be quickly adjusted to thereby attain a correct focal length position and perform the focus tracking of a workpiece continuously, so as to ensure that clear images can be taken of the workpiece.

2. According to the present invention, the focal length is adjusted according to the dimensions of a predefined figure feature such that the consistency of the dimensions of the images is free from errors which might otherwise happen because of a divergence of judgments on resolution.

DETAILED DESCRIPTION OF THE INVENTION

Figure 1:
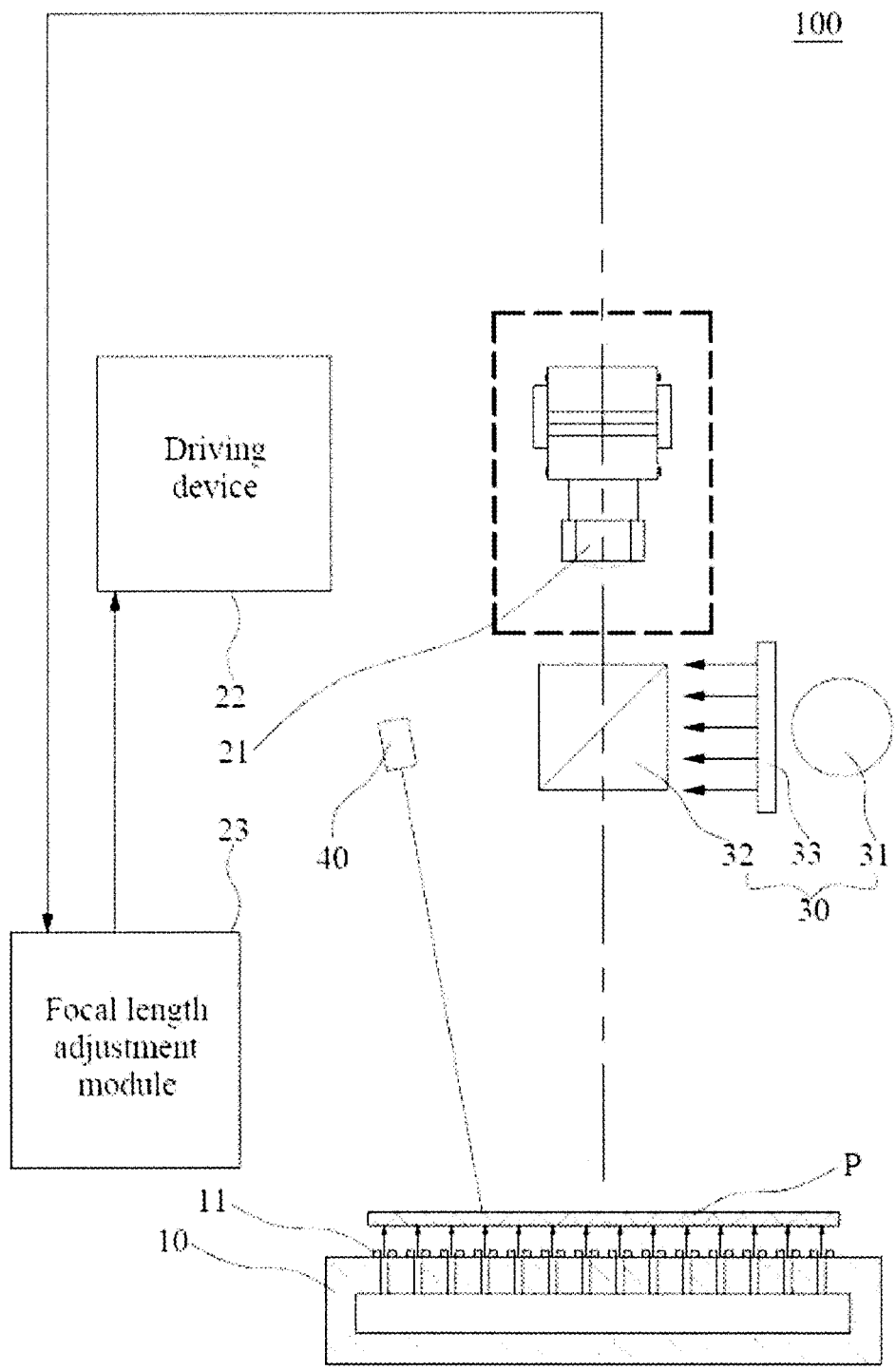
FIG. 1 is a schematic view of an automatic focus tracking system according to the first embodiment of the present invention.

The details and technical features of the present invention are depicted with drawings and described below. For illustrative sake, the drawings of the present invention are not drawn to scale. The drawings and the proportions of figures in the drawings are not restrictive of the scope of the present invention.

An automatic focus tracking system of the present invention is applicable to a table for use in automated optical inspection to operate in conjunction with an image capturing device (CCD, CMOS camera) in performing precision inspection of a workpiece, such as MEMS components (such as semiconductor devices and chips), panels, wafers or the like. The technical features of the automatic focus tracking system of the present invention are depicted with drawings and described below.

Referring to FIG. 1, there is shown a schematic view of an automatic focus tracking system 100 according to the first embodiment of the present invention.

The automatic focus tracking system 100 comprises: a gas platform 10 for carrying a workpiece P; an image capturing device 21 disposed beside the gas platform 10 and defining a target region; a driving device 22 disposed beside the image capturing device 21; a focal length adjustment module 23 coupled to the image capturing device 21 and the driving device 22; and a light module 30 disposed between the image capturing device 21 and the target region to provide coaxial light.

The gas platform 10 provides the workpiece P with a positive pressure under which the workpiece P is suspended above the gas platform 10. An air pressure pump (not shown) is disposed beside the gas platform 10 to provide a positive pressure to a plurality of nozzles 11 on the gas platform 10; hence, the air emitted from the nozzles 11 drifts upward under the positive pressure to suspend the workpiece P above the gas platform 10. In a preferred embodiment, the gas platform 10 is fixed to an edge of the workpiece P with a jig to move the workpiece P horizontally, thereby conveying the workpiece P. In another preferred embodiment, the direction in which the nozzles 11 are pointed at is changed in a manner to subject the workpiece P to a horizontal component of force under which the workpiece P advances. The present invention is not limited to the aforesaid embodiments.

The image capturing device 21 follows the workpiece P moving upward or downward to ensure that the workpiece P can be focused with reasonable focus range. The image capturing device 21 is a charge-coupled device (CCD) or a complementary metal oxide semiconductor (CMOS) device, but the present invention is not limited thereto.

The driving device 22 is coupled to the image capturing device 21 to adjust the height of the image capturing device 21 and thus control the spacing between the image capturing device 21 and the workpiece P. In a preferred embodiment, the driving device 22 uses a servo motor to rotate a screw whereby a platform carrying the image capturing device 21, the light module 30 and an optical projector 40 undergoes upward or downward displacement. Due to the insignificant extent of its errors, the servo motor can adjust precisely the height of the image capturing device 21 according to the position of the workpiece P.

The focal length adjustment module 23 captures an image of the workpiece P through the image capturing device 21, locks a predefined figure feature Q in the image of the workpiece P, and adjusts the position of the image capturing device 21 through the driving device 22, so that the figure feature Q corresponds in dimension to a predefined figure feature, thereby effectuating real-time focus tracking. A computation process performed with the focal length adjustment module 23 is discussed later.

According to the present invention, the figure feature Q is a figure or pattern on the surface of the workpiece P, or the shape of an electrode. Alternatively, the figure feature Q can be projected onto the workpiece P or the vicinity of the workpiece P by laser or any other optical means, and thus the projected image of the figure feature Q serves as a reference figure for use by the focal length adjustment module 23 in focusing. In this embodiment, the optical projector 40 is provided and adapted to project the figure feature Q onto the workpiece P or the vicinity of the workpiece P.

The light module 30 is disposed between the image capturing device 21 and the target region to illuminate the workpiece P. The light module 30 comprises an illumination unit 31 disposed beside the image capturing device 21 and a spectroscope 32 disposed between the image capturing device and the target region to reflect the light of the illumination unit 31 on the gas platform 10 to form the coaxial light. The spectroscope 32, which tilts at 45 degrees, allows a portion of the light emitted from the illumination unit 31 to bend downward by 90 degrees and thus illuminate the workpiece P. Furthermore, an image of the workpiece P is passed through the spectroscope 32, so as for the image to be sent to and thus captured by the image capturing device 21. In a preferred embodiment, the light module 30 comprises a diffuser 33 disposed between the spectroscope 32 and the illumination unit 31. The light emitted from the illumination unit 31 is rendered uniform by the diffuser 33 to prevent the formation of bright bands and dark bands.

The computation process performed with the focal length adjustment module 23 is discussed below.

Figure 2:
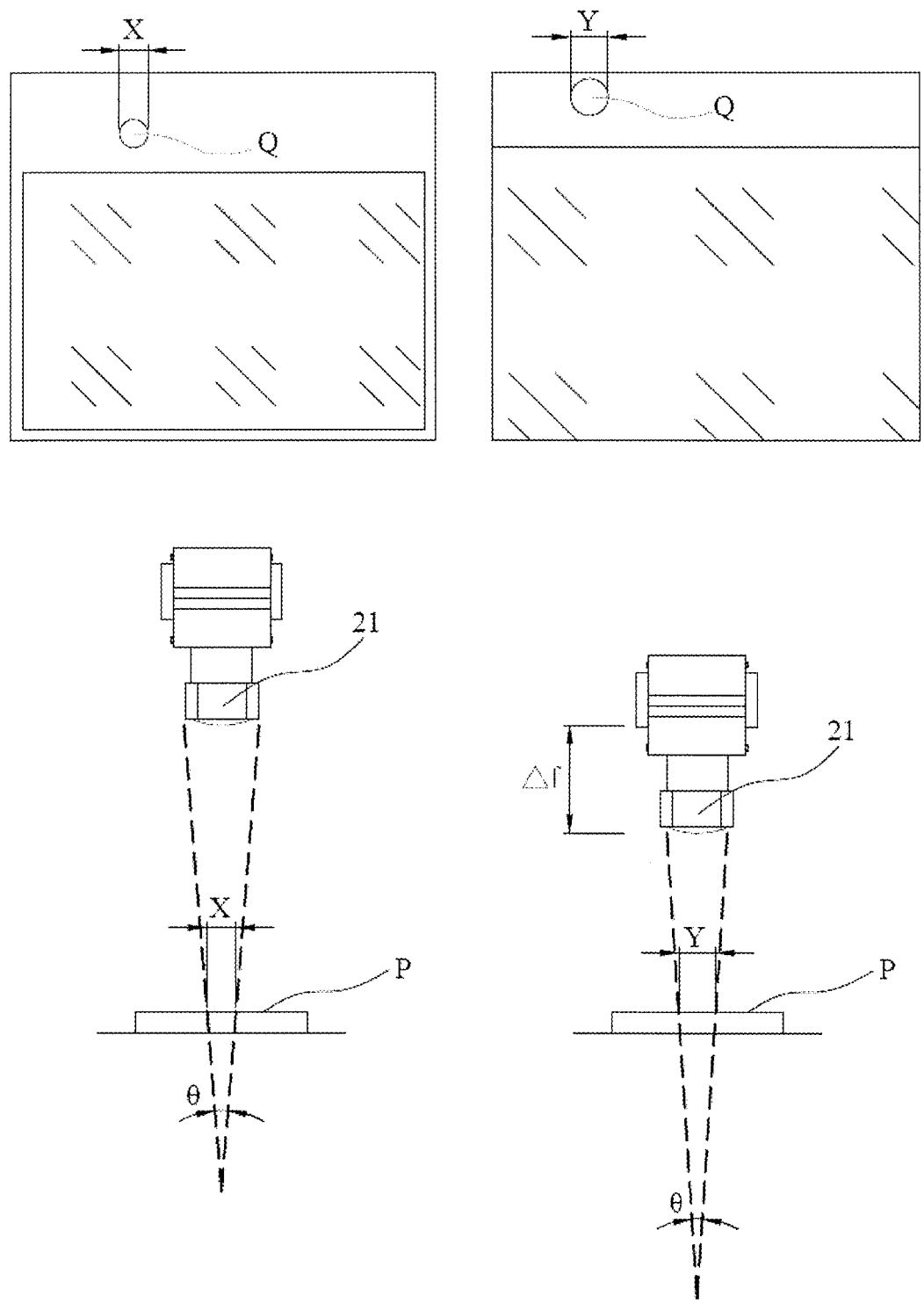
FIG. 2 is a schematic view of operation of automatic focusing according to the present invention.

Referring to FIG. 2, to carry out initial configuration, the focal length adjustment module 23 captures preliminarily, through predefinition (whether by hand or by image correction), an image of the workpiece P to be inspected, retrieves the figure feature Q (such as a pattern or figure on the surface of the workpiece P or a figure optically projected) from the image of the workpiece P, and stores related parameter (such as radius, length, or area) of the figure feature Q and the figure feature Q in a storage unit to serve as reference data.

To carry out focus tracking, the image capturing device 21 captures an image of the workpiece P, locks the predefined figure feature in the image of the workpiece P, and adjusts the position (height) of the image capturing device 21, so that the predefined figure feature has a predefined dimension, thereby effectuating focusing.

In a preferred embodiment, the focal length adjustment module 23 computes the area of the figure feature Q in real time so as to move the image capturing device 21 and thus attain a correct focal length. The image capturing device 21 finds the predefined figure feature in the image and retrieves the figure feature Q. The dimensions (radius, length, or area) of the figure feature Q thus retrieved are analyzed by real-time computation. If the dimensions of the figure feature Q are less than a pre-stored parameter, the focal length adjustment module 23 will controllably drive the image capturing device 21 to move upward and thus cause the focus of the image capturing device 21 to move upward. Conversely, if the dimensions of the figure feature Q are larger than the pre-stored parameter, the focal length adjustment module 23 will drive the image capturing device 21 to move downward and thus cause the focus of the image capturing device 21 to move downward. The aforesaid movement of the image capturing device 21 is accompanied by the real-time computation of the area of the figure feature Q in order to analyze and determine whether the image capturing device 21 has reached a predetermined focusing position, thereby effectuating real-time dynamic automatic focus tracking.

In another preferred embodiment, the focal length adjustment module 23 uses the ratio of the figure feature Q to the predefined figure to calculate a distance between the image capturing device 21 and the correct focal length position as a distance parameter, whereas the driving device 22 drives the image capturing device 21 to move to the correct focal length position according to the distance parameter.

Referring to FIG. 2, once the figure feature Q on the workpiece P is focused clearly by the image capturing device 21, an optical mark pattern corresponding in dimension to the predefined figure feature will be produced. However, in the situation where the image capturing device 21 is defocusing, the optical projector 40 does not project the figure feature Q onto a focusing surface of the workpiece P, and in consequence a defocused pattern is produced. The dimension of the predefined figure feature is denoted by x. The dimension attributed to the figure feature Q shot and computed is denoted by y. Due to a linear relationship in a feature diameter between a focused pattern and a defocused pattern, a coefficient can be converted into a difference in the operating distance of the focusing surface. C denotes the linear coefficient between the operating distance and the feature diameter, wherein the coefficient is a constant under the same focus tracking system (i.e., the same ambient condition) and can be obtained by conducting a practical test. Hence, the distance $\Delta f$ between the correct focal length positions are calculated by the equation below.

$$\Delta f = C(x-y)$$

A positive value of the calculated distance $\Delta f$ indicates that the image capturing device 21 must move downward by a distance of $|\Delta f|$ in order to zoom in the image and move the image to the correct focal length position. A negative value of the calculated distance $\Delta f$ indicates that the image capturing device 21 must move upward by a distance of $|\Delta f|$ in order to zoom out the image and move the image to the correct focal length position.

Therefore, the image capturing device 21 can be quickly moved to the correct focal length position to effectuate real-time focusing.

Figure 3:
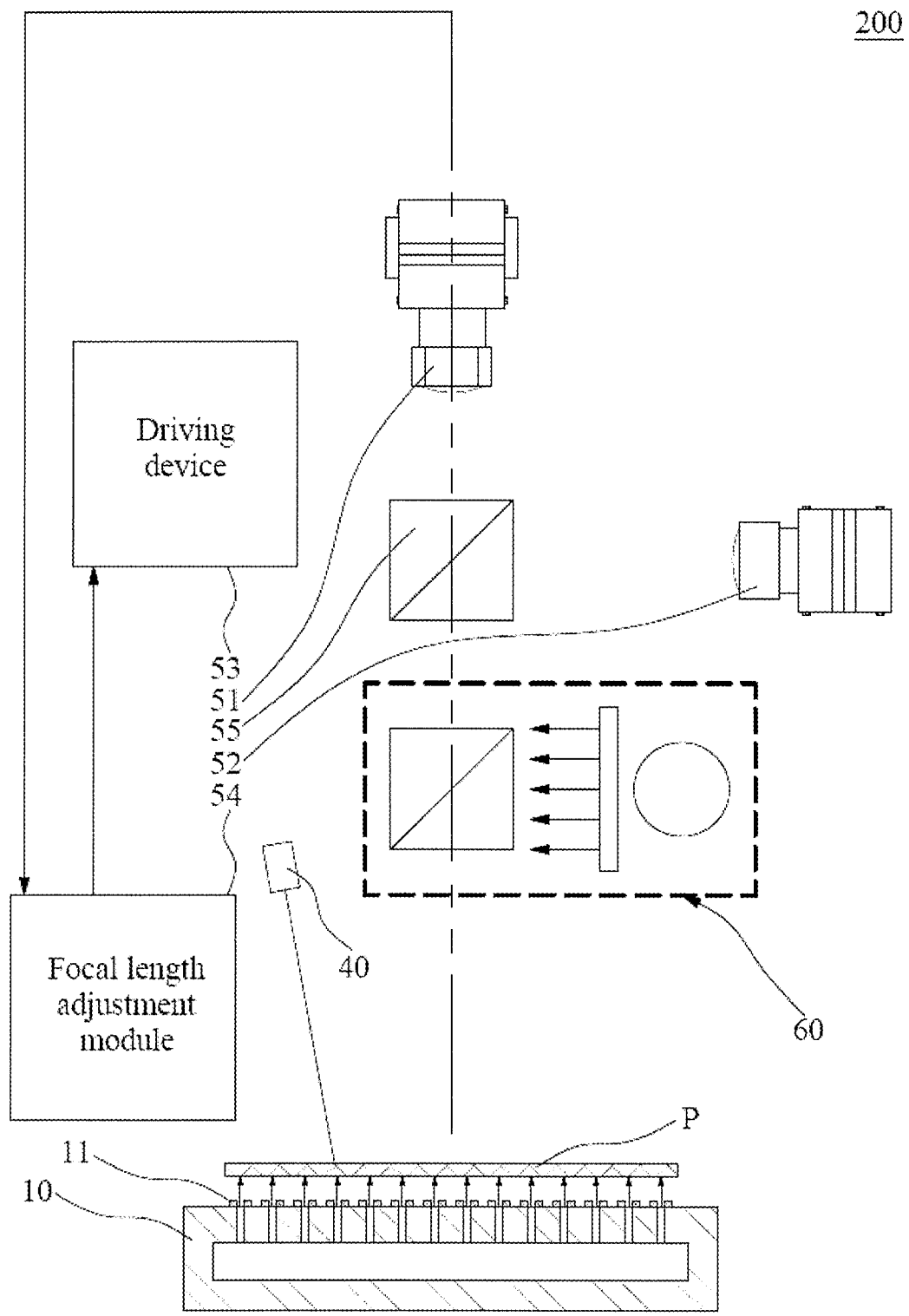
FIG. 3 is a schematic view of an automatic focus tracking system according to the second embodiment of the present invention.

Referring to FIG. 3, there is shown a schematic view of an automatic focus tracking system 200 according to the second embodiment of the present invention. The second embodiment of the present invention differs from the first embodiment of the present invention in that an image capturing device in the first embodiment of the present invention is divided into two groups, one for inspecting a workpiece for defects thereof, and other for calculating the spacing of the workpiece.

In the second embodiment of the present invention, the automatic focus tracking system 200 comprises: a first image capturing device 51 for obtaining an image of a workpiece in a target region; a second image capturing device 52 for obtaining the figure feature Q on the workpiece P or in the vicinity of the workpiece P; a driving device 53 for adjusting the spacing between the first image capturing device 51 and the workpiece P; and a focal length adjustment module 54 connected to the driving device 53 and the second image capturing device 52. The focal length adjustment module 54 generates and sends a control signal to the driving device 53 according to a predefined figure feature in an image of the workpiece P. The control signal drives the driving device 53 to adjust the position of the first image capturing device 51.

In the second embodiment, the first image capturing device 51 and the second image capturing device 52 are fixed to the same platform, controlled by the focal length adjustment module 54, and moved through a screw. The optical path of the workpiece P goes from a spectroscope 55 to the first image capturing device 51 and the second image capturing device 52. The light module 60 is disposed below the spectroscope 55. The optical projector 40 is disposed beside the gas platform 10. Both the light module 60 and the optical projector 40 move upwardly or downwardly (when disposed on the same platform, for example) together with the first image capturing device 51 and the second image capturing device 52 to maintain a fixed spacing between the light module 60, the optical projector 40, the first image capturing device 51 and the second image capturing device 52, and in consequence all the images shot are equal in brightness and sharpness. To effectuate focusing, the second image capturing device 52 detects and calculates in real time a focusing value (difference) which the optical projector 40 retrieved from the figure feature Q on the workpiece P, and then the focusing value is used by the motor in controllably moving the first image capturing device 51, the second image capturing device 52, the light module 60 and the optical projector 40 until the focusing value meets an expectation.

In another preferred embodiment, the second image capturing device 52 and the first image capturing device 51 are disposed on different platforms, respectively. The first image capturing device 51 is movable, whereas the second image capturing device 52 is stationary. The spectroscope 55 is disposed between the first image capturing device 51 and the second image capturing device 52. The first image capturing device 51 moves straight along the optical path of the spectroscope 55 to adjustably move the first image capturing device 51 to the focal length position. Both the light module 60 and the optical projector 40 move upwardly or downwardly together with the first image capturing device 51 (when disposed on the same platform, for example) such that all the images shot are equal in brightness and sharpness. The second image capturing device 52 compares the figure feature Q with a predefined dimension, calculates a focusing value (difference value), and sends the focusing value (difference value) to the focal length adjustment module 54. The focal length adjustment module 54 controls the positions of the first image capturing device 51, the light module 60 and the optical projector 40 according to the focusing value until the focusing value meets an expectation, thereby effectuating dynamic automatic focus tracking.

In conclusion, a computation process of the present invention is simple enough to enable an image capturing device to be quickly adjusted to thereby attain a correct focal length position and perform the dynamic automatic focus tracking of a workpiece continuously, so as to ensure that clear images can be taken of the workpiece. Furthermore, according to the present invention, the focal length is adjusted according to the dimensions of a predefined figure feature such that the consistency of the dimensions of the images is free from errors which might otherwise happen because of a divergence of judgments on resolution.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. A dynamic automatic focus tracking system, comprising:
    an image capturing device pointed at a picture-taking region to perform an image-capturing process on a workpiece and thus capture an image of the workpiece;
    a driving device for adjusting a spacing between the image capturing device and the workpiece; and
    a focal length adjustment module coupled to the image capturing device and the driving device to generate a control signal according to a figure feature and a predefined figure feature in the image of the workpiece and send the control signal to the driving device, thereby adjusting a position of the image capturing device with the driving device;
    wherein the focal length adjustment module calculates a distance parameter between the image capturing device and a correct focal length position according to a ratio of the figure feature to the predefined figure feature and controls the driving device according to the distance parameter, thereby allowing the image capturing device to move to the correct focal length position.

2. The dynamic automatic focus tracking system of claim 1, further comprising a gas platform for providing the workpiece with a positive pressure under which the workpiece is suspended above the gas platform.

3. The dynamic automatic focus tracking system of claim 1, further comprising an optical projector for projecting the figure feature onto the workpiece or to a vicinity of the workpiece.

4. The dynamic automatic focus tracking system of claim 1, further comprising a light module disposed between the image capturing device and the picture-taking region to provide coaxial light.

5. The dynamic automatic focus tracking system of claim 4, wherein the light module comprises an illumination unit disposed beside the image capturing device and a spectroscope disposed between the image capturing device and the picture-taking region to reflect light off the illumination unit such that the light falls on the picture-taking region to form the coaxial light.

6. A dynamic automatic focus tracking system, comprising:
    a first image capturing device pointed at a picture-taking region to perform an image-capturing process on a workpiece and thus capture an image of the workpiece;
    a second image capturing device for locking a figure feature on the workpiece or near the workpiece;
    a driving device for adjusting a spacing between the first image capturing device and the workpiece; and
    a focal length adjustment module coupled to the second image capturing device and the driving device to generate a control signal according to a figure feature and a predefined figure feature in the image of the workpiece and send the control signal to the driving device, thereby adjusting a position of the first image capturing device with the driving device;
    wherein the focal length adjustment module calculates a distance parameter between the first image capturing device and a correct focal length position according to a ratio of the figure feature to the predefined figure feature and controls the driving device according to the distance parameter, thereby allowing the first image capturing device to move to the correct focal length position.

7. The dynamic automatic focus tracking system of claim 6, further comprising a gas platform for providing the workpiece with a positive pressure under which the workpiece is suspended above the gas platform.

8. The dynamic automatic focus tracking system of claim 6, further comprising an optical projector for projecting the figure feature onto the workpiece or to a vicinity of the workpiece.

9. The dynamic automatic focus tracking system of claim 6, further comprising a light module disposed between the first image capturing device and the picture-taking region to provide coaxial light.

10. The dynamic automatic focus tracking system of claim 9, wherein the light module comprises an illumination unit disposed beside the first image capturing device and a spectroscope disposed between the first image capturing device and the picture-taking region to reflect light off the illumination unit such that the light falls on the picture-taking region to form the coaxial light.

* * * * *